US009282944B2

(12) United States Patent
Fallavollita et al.

(10) Patent No.: US 9,282,944 B2
(45) Date of Patent: Mar. 15, 2016

(54) C-ARM POSE ESTIMATION USING INTENSITY-BASED REGISTRATION OF IMAGING MODALITIES

(75) Inventors: Pascal Fallavollita, Munich (DE); Gabor Fichtinger, Kingston (CA); Purang Abolmaesumi, Vancouver (CA); E. Clif Burdette, Champaign, IL (US)

(73) Assignee: QUEEN'S UNIVERSITY AT KINGSTON, Kingston, Ontario (CA)

( * ) Notice: Subject to any disclaimer, the term of this patent is extended or adjusted under 35 U.S.C. 154(b) by 96 days.

(21) Appl. No.: 13/165,990

(22) Filed: Jun. 22, 2011

(65) Prior Publication Data
US 2011/0313285 A1 Dec. 22, 2011

Related U.S. Application Data

(60) Provisional application No. 61/357,455, filed on Jun. 22, 2010.

(51) Int. Cl.
| | |
|---|---|
| *A61B 6/00* | (2006.01) |
| *A61B 19/00* | (2006.01) |
| *A61N 5/10* | (2006.01) |
| *G06T 7/00* | (2006.01) |
| *A61B 17/00* | (2006.01) |
| *A61B 18/00* | (2006.01) |

(52) U.S. Cl.
CPC ............... *A61B 6/547* (2013.01); *A61B 6/4441* (2013.01); *A61B 19/52* (2013.01); *A61B 19/54* (2013.01); *A61N 5/1001* (2013.01); *G06T 7/0026* (2013.01); *G06T 7/0044* (2013.01); *A61B 6/487* (2013.01); *A61B 2017/00274* (2013.01); *A61B 2018/00547* (2013.01); *A61B 2019/5289* (2013.01); *A61B 2019/5466* (2013.01); *G06T 2207/10072* (2013.01); *G06T 2207/10121* (2013.01); *G06T 2207/10124* (2013.01); *G06T 2207/10136* (2013.01); *G06T 2207/30081* (2013.01); *G06T 2207/30204* (2013.01)

(58) Field of Classification Search
CPC .................. A61B 19/52; A61B 19/54; A61B 2017/00274; A61B 2018/00547; A61B 2019/5289
USPC ................... 600/407, 426, 442, 410; 382/128
See application file for complete search history.

(56) References Cited

U.S. PATENT DOCUMENTS

| | | | | | |
|---|---|---|---|---|---|
| 6,837,892 | B2* | 1/2005 | Shoham | ......................... | 606/130 |
| 7,474,913 | B2* | 1/2009 | Durlak | ......................... | 600/428 |
| 7,940,999 | B2* | 5/2011 | Liao et al. | ..................... | 382/294 |
| 8,131,041 | B2* | 3/2012 | Ter Mors | ...................... | 382/131 |
| 2001/0029334 | A1* | 10/2001 | Graumann et al. | ............ | 600/437 |
| 2004/0024302 | A1* | 2/2004 | Chalana et al. | ............... | 600/407 |
| 2004/0151356 | A1* | 8/2004 | Li et al. | ......................... | 382/131 |
| 2007/0053605 | A1* | 3/2007 | Ritter et al. | .................... | 382/260 |

(Continued)

OTHER PUBLICATIONS

Jain, A.K. et al., "FTRAC—a robust fluoroscope tracking fiducial." Medical physics; 32(10), pp. 3185-3198, 2005.

(Continued)

*Primary Examiner* — Baisakhi Roy

(57) ABSTRACT

This invention provides a method for estimating C-arm fluoroscope pose. The method involves introducing a coordinate system into a C-arm image, and applying intensity-based 2D/3D registration without segmentation to the coordinate system C-arm image and an image or known model of the coordinate system, wherein the intensity-based 2D/3D registration yields the C-arm pose. The coordinate system may be provided by introducing one or more markers or a fiducial into an image.

22 Claims, 4 Drawing Sheets

(56) References Cited

U.S. PATENT DOCUMENTS

| | | | |
|---|---|---|---|
| 2008/0262345 A1* | 10/2008 | Fichtinger et al. | 600/426 |
| 2009/0281452 A1* | 11/2009 | Pfister et al. | 600/567 |
| 2009/0290771 A1* | 11/2009 | Frank et al. | 382/128 |
| 2009/0326373 A1* | 12/2009 | Boese et al. | 600/440 |
| 2010/0189367 A1* | 7/2010 | van der Merwe et al. | 382/217 |
| 2011/0096907 A1* | 4/2011 | Mohamed | 378/98 |
| 2011/0152676 A1* | 6/2011 | Groszmann et al. | 600/426 |
| 2011/0200238 A1* | 8/2011 | Garud et al. | 382/128 |

OTHER PUBLICATIONS

Jain, A.K. et al., "Intra-operative Guidance in Prostate Brachytherapy Using an Average Carm." MICCAI 2007, Lecture Notes in Computer Science, 4792, pp. 9-16, 2007.

Nithiananthan, S. et al., "Deformable registration for intra-operative cone-beam CT guidance of head and neck surgery," IEEE Proceedings of Engineering in Medicine and Biology Society, 1, pp. 3634-3637, 2008.

Lee, J. et al.: Prostate brachytherapy seed reconstruction with Gaussian 590 blurring and optimal coverage cost. IEEE Trans Med Imaging, 28(12):1955-68 (2009).

Mattes, D. et al., "PET-CT image registration in the chest using free-form deformations," IEEE Trans. Medical Imaging, 22(1):120-128 (2003).

Mattes, D. et al., Nonrigid multimodality image registration. Proc. SPIE Medical Imaging: pp. 1609-1620, 2001.

* cited by examiner

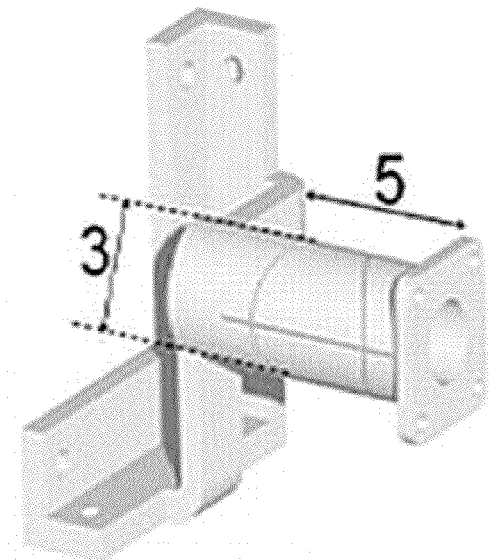
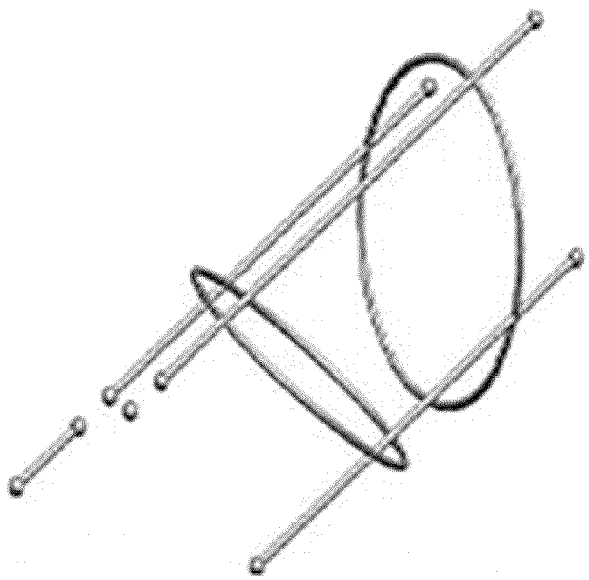
Figure 1A    Figure 1B
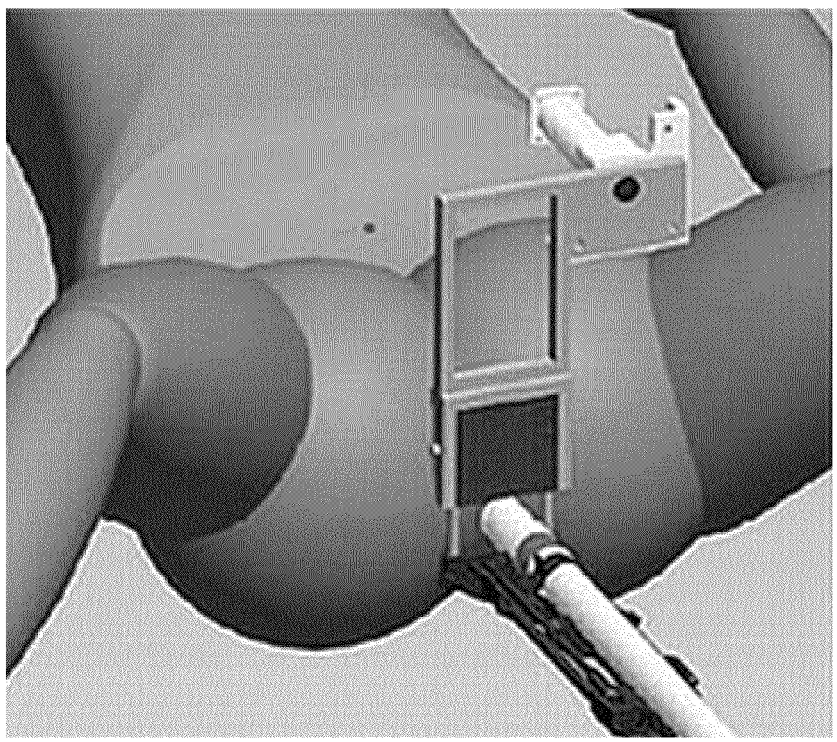
Figure 1C

Step 1: C-arm image pre-processing.

Step 2: DRR generation of fiducial.

Step 4: CMA-ES computes new Euler 3D parameters.

Step 3: Compute NCC metric.

C-ARM POSE ESTIMATION USING INTENSITY-BASED REGISTRATION OF IMAGING MODALITIES

RELATED APPLICATION

This application claims the benefit of the filing date of U.S. Provisional Patent Application No. 61/357,455, filed on 22 Jun. 2010, the contents of which are incorporated herein by reference in their entirety.

FIELD OF THE INVENTION

This invention relates to methods and systems for improving accuracy of clinical procedures that rely on C-arm fluoroscopy images. In embodiments of the methods and systems described herein the relative pose of C-arm images may be estimated by registering image data from imaging modalities using markers or a fiducial. The embodiments described herein are particularly useful in brachytherapy procedures.

BACKGROUND

Although C-arm fluoroscopy is widely used for visual assessment during clinical procedures, a limitation is that it cannot show soft tissues or organs of interest and other relevant structures. On the other hand, use of other imaging modalities such as ultrasound during clinical procedures provides real-time visualization of the tissue/organ of interest but does not provide radiographic information. Fusion of these complementary imaging modalities would provide benefits during many procedures.

For example, interventional tool registration with soft tissue would benefit from being able to accurately view the tool and the soft tissue of interest simultaneously during a medical procedure. The procedure could be performed with greater precision through improved tool visualization and registration with the soft tissues undergoing the procedure. Further, the ability to visualize the soft tissue using another imaging modality such as ultrasound provides real time information to the clinician performing the procedure.

Brachytherapy is such a procedure. Brachytherapy involves the placement of radioactive pellets or "seeds" into or adjacent cancerous tissue of a patient. Brachytherapy makes it possible to treat the cancer with a high total dose of radiation in a concentrated area in a short period of time, and at the same time spare healthy tissues the treatment with radiation. The key to successful brachytherapy is the accurate placement of the seeds. However, faulty needle and seed placement often cause an insufficient dose to the cancer and/or inadvertent radiation of healthy tissues. The ability to perform dosimetry optimization during the procedure could change the standard of care in brachytherapy, but such function is not available today and it is unfortunate that implants are currently performed without an explicit dosimetry evaluation in the operating room. Generally, dosimetric analysis requires precise localization of the implanted seeds in relation to the cancerous tissue and surrounding anatomy.

Brachytherapy may be performed with ultrasound guidance that provides real-time visualization of the tissue/organ of interest but not of the implanted seeds for a variety of reasons, including but not limited to scattering from implanted seeds, noise in the image, and shadowing caused by implanted seeds. C-arm fluoroscopy, on the other hand, is widely used for gross visual assessment of the implanted seeds but it cannot sufficiently image the soft tissue/organ and other relevant structures. Fusion of these complementary modalities would enable dynamic dosimetry, wherein the dose distribution is updated dynamically based on the actual positions as the seeds are deposited. For fusion of these modalities, 3D reconstruction of the seeds is necessary and requires that the relative poses of the fluoroscopy images must be known prior to reconstruction.

Pose recovery on C-arm fluoroscopy machines is a major technical problem that presently does not have a clinically practical solution in many areas of application. Currently, the relative poses of fluoroscopy images are determined in one of following three ways: (i) electronic joint encoders, (ii) optical or electromagnetic tracker, and (iii) radiographic fiducials. Fully encoded C-arm fluoroscopes are very expensive and thus virtually non-existent in brachytherapy. External trackers are also impractical for various reasons and also add costs. Optical tracking (e.g., VectorVision® Navigation System, "Brainlab, Inc., Heimstetten, Germany; StealtStation®, Medtronic Surgical Navigation Technologies, Louisville, Colo., USA) requires line of sight which imparts alterations in clinical setup and workflow. Electromagnetic tracking (e.g., OEC 9800 FluoroTrak™, GE Healthcare, Waukesha, Wis., USA) overcomes these issues, but it is susceptible to field distortion from metal objects, such as the C-arm itself, and thus compromise on accuracy.

Several researchers have explored fiducial-based radiographic tracking [1-4]. In an effort to make fiducials better integrated in the clinical setup, compact fiducials have been explored. However, decreasing the size of the fiducial fixture also decreases tracking accuracy. In fiducial structures made up of beads, 1-3 mm translation accuracy and 1°-2° orientation accuracy in tracking the C-arm has been achieved [2-4]. For prostate brachytherapy Jain et al. developed a fluoroscope tracking (FTRAC) fiducial [5] and validated the device clinically [6]. The fiducial used spherical beads and straight lines and ellipses that are invariant to projection, in that they project as straight lines and ellipses (see FIG. 1B). However, the technique involved segmentation of different features of the FTRAC fiducial in C-arm images, which was found to be fragile in actual field practice [6].

SUMMARY

Provided herein are methods and systems for estimating C-arm pose. In the methods and systems described herein the relative pose of C-arm images may be estimated by registering image data from one or more imaging modalities using markers or a fiducial of known geometry. In one embodiment the image data are from the same imaging modality.

Described herein is a method for estimating C-arm pose, comprising: introducing a coordinate system into a C-arm image; and registering the coordinate system C-arm image and an image or known model of the coordinate system using a registration method; wherein the registration yields the C-arm pose.

In one embodiment the method may comprise: introducing a coordinate system into a C-arm image; and applying intensity-based 2D/3D registration without segmentation to the coordinate system C-arm image and an image or known model of the coordinate system; wherein the intensity-based 2D/3D registration yields the C-arm pose.

Applying intensity-based registration may include comparing a 2D C-arm image with a 3D image reconstructed from an image volume. The image volume may be obtained using an imaging modality selected from ultrasound, X-ray, CT, and MRI. The coordinate system may be provided by introducing one or more markers. Introducing one or more markers may be associated with a therapeutic procedure or a medical intervention. Introducing one or more markers may include implanting, attaching, or fixing one or more markers to a tissue or an organ of interest. One embodiment may include iteratively updating locations of markers and using those marker locations to compute pose. In another embodiment the coordinate system may be provided by introducing a fiducial.

Intensity based registration may include filtering the C-arm image to simultaneously enhance coordinate system features and suppress neighbouring structures. Filtering the C-arm image may comprise using one or more filters or applying a three-step filter and a line enhancement filter. The three-step filter may include a morphological filter, a homomorphic filter, and a complex shock filter. Processing images may comprise applying an imaging-blurring filter.

The images may be associated with a medical intervention. The C-arm images may include markers. The markers may be selected from radioactive seeds and surgical clips. In one embodiment the images are associated with a brachytherapy procedure. The brachytherapy procedure may be associated with treating prostate cancer.

Also described herein is programmed media for use with a computer and with C-arm image data and ultrasound, X-ray, CT, or MRI image data, the image data including a coordinate system, the programmed media comprising: a computer program stored on storage media compatible with the computer, the computer program containing instructions to direct the computer to: apply intensity-based 2D/3D registration without segmentation to the coordinate system C-arm image and an image or known model of the coordinate system, wherein the intensity-based registration yields the C-arm pose; and output an indication of the C-arm pose.

BRIEF DESCRIPTION OF THE DRAWINGS

For a better understanding of the invention, and to show more clearly how it may be carried into effect, embodiments will now be described, by way of example, with reference to the accompanying drawings, wherein:

FIG. 1A shows a cylindrical sheath design, and FIG. 1B shows a wire model, of a specific instance of a fluoroscopy tracking (FTRAC) fiducial. FIG. 1C shows a radiographic fiducial of size 3×5 cm attached to the needle insertion template during intervention.

DETAILED DESCRIPTION OF EMBODIMENTS

Figure 2:
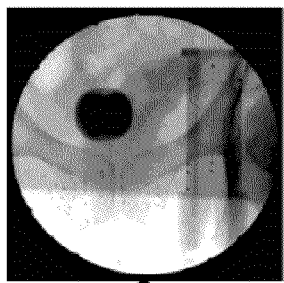
FIG. 2 is a flowchart showing a C-arm pose recovery method according to one embodiment.
Figure 2:
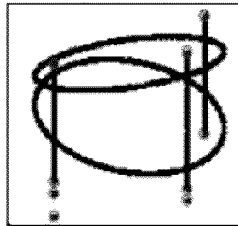
Figure 2:
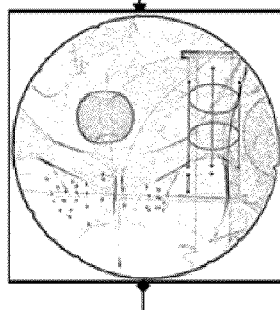
Figure 2:
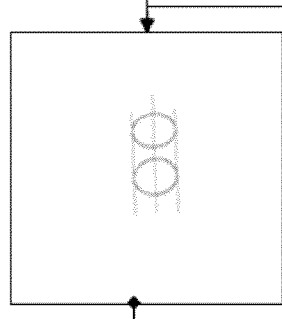
Figure 2:
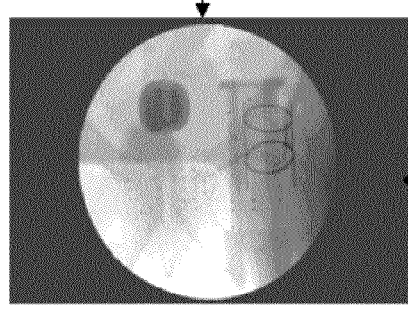

In the embodiments described herein, the relative pose of a C-arm fluoroscopy image is estimated by registration of the 2D fluoroscopy image to a 3D image volume. The 3D image volume may be generated by ultrasound or other suitable imaging technology. The pose of the C-arm images is estimated using a coordinate system fixed to the tissue/organ of interest. This allows the C-arm pose to be estimated with an accuracy that is sufficient for subsequent reconstruction of the implanted seeds and thus enable 2D/3D intensity based registration. In one embodiment the coordinate system may be established through use of a fiducial. In another embodiment the coordinate system may be established by one or more markers implanted in or otherwise attached or fixed to the tissue/organ of interest. For example, one or more of numerous imaging techniques may be used to accurately determine the placement of seeds during a brachytherapy procedure. These seeds represent the equivalent of a fiducial to subsequent modifications of C-arm pose. In this manner, dynamic pose estimation during a procedure may be carried out by iteratively updating the locations of seeds and using those seed locations to compute pose.

Algorithms for 2D/3D registration of 2D radiographic projections to 3D CT images can be broadly categorized as feature-based methods, methods that use intensity-derived features, intensity-based methods, and hybrid methods. Feature based methods use distance between corresponding point pairs or surfaces as a measure to be optimized. Establishing point correspondences and minimizing the distance between them is alternated and repeated iteratively until convergence. Consequently, prior segmentation of the image data is required. Intensity-based methods compare the 2D image with a digitally reconstructed radiograph (DRR) created from the 3D volume. Key to intensity-based registration is the choice of an appropriate similarity measure to quantify the spatial alignment between the images. An understanding of the image formation process and the underlying relationship between intensity values in the modalities being matched is often useful in choosing the similarity measure. The hybrid registrations usually exploit both image and geometric information and are based on two alternated registrations.

As described herein, the relative pose of a C-arm fluoroscopy image is estimated by registering the fluoroscopy image to a fiducial or marker image without segmentation. In particular, intensity-based registration techniques as described herein do not require prior segmentation, a substantial improvement over segmentation-based registration that usually requires some level of manual intervention and is hampered by segmentation errors. Intensity-based registration may use the entire image volumes and thus both false positive and false negative appearances may average out.

As used herein, the term "intensity" refers to the amplitude, pixel value, or probability score, or derivative thereof, such as a value derived from the intensity (e.g., image gradient), or combination thereof, of the markers or seeds in the images.

As used herein, the terms "marker" and "seed" are interchangeable and refer to a feature in a material that may be resolved with an imaging technology. Markers or seeds may include a feature already present in the material, such as an inherent part of the material, a feature implanted in the material, a feature attached or fixed to the material, or combinations thereof. Markers or seeds may be man-made or naturally occurring. For example, a marker may be a radioactive seed as used during a brachytherapy procedure, a surgical clip, or any other suitable material or device.

One application of the embodiments described herein is in brachytherapy. Brachytherapy may be performed with ultrasound guidance that provides real-time visualization of the tissue/organ of interest but not of the implanted seeds. C-arm fluoroscopy, on the other hand, may be used for visual assessment of the implanted seeds but it cannot show the tissue/organ and other relevant structures. Fusion of these complementary modalities would enable dynamic dosimetry. For fusion of these modalities, 3D reconstruction of the seeds is necessary and requires that the relative poses of the fluoroscopy images must be known prior to reconstruction. Embodiments described herein provide accurate reconstruction of brachytherapy seed placement, although use of the embodiments is not limited thereto.

In one embodiment the C-arm pose may be recovered adequately using a 2D/3D intensity-based registration algorithm between the fiducial C-arm image and the fiducial's known geometrical model. To demonstrate one embodiment, the fluoroscope tracking (FTRAC) fiducial introduced by Jain et al. [5] (see FIG. 1) was used. However, it will be appreciated that the invention described herein is not limited to use of radiographic fiducials such as the FTRAC. Rather, other fiducials may be used, or markers may be used as fiducials. For example, one or more markers implanted in or otherwise attached or fixed to the tissue/organ of interest may effectively serve as a fiducial. Imaging technologies that may be used to generate fiducial images, depending, e.g., on the characterisitics of the fiducial, include, but are not limited to, ultrasound (e.g., TRUS, A-mode, B-mode, M-mode, Doppler, and 3D), X-ray (e.g., 2D X-ray, fluoroscopy, CT, or a 2D projection of a volume derived from CT), and MRI or a 2D projection of a volume derived from MRI.

As used herein, the term "projection" refers to a 2D image generated from a volume by a ray-casting or ray-tracing technique, or a derivative thereof.

The FTRAC fiducial includes spherical beads, straight lines, and ellipses that are invariant to projection, in that they project as straight lines and ellipses (FIG. 1B). Such parametric curves segment accurately and constrain the optimization during pose recovery, allowing for a mean accuracy of 0.56±0.33 mm in translations and 0.33°±0.21° in rotations. The FTRAC design has small dimensions (3×3×5 cm), no special proximity requirements to the anatomy, and is relatively inexpensive. Jain et al. [5] mounted the FTRAC fiducial over the seed insertion needle template using a mechanical connector (FIG. 1C). After semiautomatic segmentation of the FTRAC fiducial in all C-arm images, the implanted seeds were reconstructed in 3D, registered with transrectal ultrasound space and sent back to the treatment planning system for dosimetric evaluation. In this prior process, the single point of failure was segmentation of the FTRAC. Sequential semi-automated segmentation of different features of the FTRAC was found to be fragile in actual field practice.

While the embodiments described herein relate primarily to prostate brachytherapy, it will be appreciated that the invention is not limited thereto. The embodiments may be used for procedures involving or not involving brachytherapy in other biological tissues and/or organs. The brachytherapy may include, but is not limited to, high dose rate, low dose rate, and pulse dose rate brachytherapy. Further, the methods described herein may be applied to the detection, diagnosis, treatment, and/or assessment of cancer or other diseases in any biological tissues and/or organs, provided that suitable markers or seeds are available to be resolved with the imaging technologies used. The markers or seeds may be already present in the tissues, or they may be implanted in the tissues prior to or during the diagnosis, treatment, and/or assessment. Such biological tissues and organs may include, but are not limited to, female genital tract (ovary, fallopian tube, uterus, cervix and vagina), male genital tract (prostate and testis), urinary tract (kidney, ureter and prostate gland), mediastinum and heart, gastrointestinal tract (small and large intestines, liver, pancreas, gallbladder and biliary system), breast, skin, nervous system, endocrine organs (thyroid gland, adrenal gland), head and neck region, lymph nodes, soft tissue, respiratory system (including lung). Embodiments of the invention may also be used for detection, diagnosis, and/or assessment of tissue abnormalities including pathological abnormalities other than cancer, such as, but not limited to, benign tumours, infection, abscess, necrosis, and infarcts.

The embodiments described herein eliminate explicit segmentation of the fiducial from the C-arm pose tracking process. The methods may include enhancing the fiducial in the C-arm image by filtering. Various filtering schemes may be used, which may include one or more filtering steps. For example, a filtering scheme may include: (i) a 3-step filter that cascades morphology, homomorphic, and complex diffusion process, and/or (ii) a line enhancement filter that is controlled by a single parameter. Filter parameters may be estimated robustly from training images. The methods may further include registering the filtered fluoroscopy image of the fiducial to its digitally reconstructed radiograph based on image intensity alone. In this manner, a practical solution is provided for a longstanding clinical problem. The solution blends seamlessly with current clinical installations and so it could be rapidly introduced into community health care with minimal cost, thereby making a positive impact within a short time.

In one embodiment, shown in FIG. 2, the 2D/3D intensity-based registration scheme described herein may include the following steps. (1) Calibrate the C-arm explicitly or assume a sufficiently accurate model of it. (2) Filter the fluoroscopy image to simultaneously enhance FTRAC features and to suppress neighboring structures. (3) Take an initial guess for pose of the C-arm relative to FTRAC. (4) Compute a digitally reconstructed radiograph (DRR) of the FTRAC. (5) Apply blurring operator on the lines/features in the DRR. (6) Run 2D/3D optimization to compute the pose using a normalized cross correlation metric and an Evolution Strategy with Covariance Matrix Adaptation (CMA-ES) optimizer. Adjust the C-arm pose and step back to (4) until convergence is achieved or failure to converge is detected. This generic method is attuned to dealing with any radiographic fiducial images containing parametric lines or curves such as helices or ellipses.

As will be understood by one of ordinary skill in the art, images of the same material produced by two imaging modalities as described herein will not exactly match each other. That is, the images produced by the different imaging modalities are not congruent. This is because of the physical properties of the material and how it interacts with the imaging modality to produce an image. In addition, in some applications images of a material obtained with two different modalities may not be obtained simultaneously, and any change in the material from when one imaging modality is used to when the next imaging modality is used will contribute to the lack of congruency in the images. The methods described herein include rigid registration, wherein any such incongruency of the images is disregarded in aligning the images. The methods described herein also include deformable registration, wherein the image data is adjusted to overcome or compensate for any incongruency. Rigid registration requires less computation and may be preferred in applications where rapid registration is required. Deformable registration begins with rigid registration, and then performs further iterations of the registration by adjusting the data to improve the fit. However, deformable registration requires more computation and is slower than rigid registration.

In one embodiment, intensity-based registration is carried out using a volume-to-volume technique. Volume-to-volume handles scenarios where seeds are reconstructed into a continuous gray-scale volume, such as true CT or cone beam computed tomography volume. Volume-to-volume also allows for a gray-scale volume to be binarized, where each seed may be represented by more than one white voxel. Such volumes result from fluoroscopy reconstructions where seeds are considered to have length and direction. Since voxel intensity is used, an interpolator is used to evaluate moving volume intensities at non-pixel positions after applying the spatial transformation in each cycle of iteration. For this reason, the continuous TRUS may be considered as the moving volume and the binarized seed cloud as fixed volume. For the first registration, the transformation parameters are initialized with an initial guess, discussed below. Then, a similarity measure evaluates the degree of matching between the transformed moving volume and the fixed volume. The measure may be, for example, mutual information or normalized correlation.

In one example of the volume-to-volume technique, the Mattes mutual information (MMI) is used. The MMI estimates a probability density function (PDF) uniformly distributed over the intensity interval. Calculations are based on the method of Mattes et al. [10,11] where the probability density distributions are estimated using Parzen histograms. Compared to standard Mutual information, the technique involves initializing a random number generator that selects a sample of voxels used for estimating the volume histograms and the joint histogram. A feature of MMI is that it uses only two parameters: the number of samples used to estimate the PDF, and the number of histogram bins used to calculate the entropy. In one embodiment, the number of histogram bins was empirically set to 50 and the number of samples used was set to 10% of the total number of voxels making up the fixed volume. For comparative purposes, the normalized correlation (NC) was also tested. Voxel values were taken from the fixed volume and their positions were mapped to the moving volume. Values at the non-grid positions of the moving volume were interpolated using a user-selected interpolator. The correlation was normalized by the autocorrelations of both the fixed and moving volumes. Let Img1 and Img2 be the fixed and moving volume, respectively. NC computes the voxel-wise cross-correlation and normalizes it by the square root of the autocorrelation. Using a simple 2D image example:

$$NC = -1 \times \frac{\sum_{i=1}^{N} Img1_i \cdot Img2_i}{\sqrt{\sum_{i=1}^{N} Img1_i^2 \cdot \sum_{i=1}^{N} Img2_i^2}} \quad (a)$$

where $Img1_i$ and $Img2_i$ are the $i^{th}$ pixels in the two images and N is the number of pixels considered. The −1 factor is used to make the metric optimal when its minimum is reached. The optimal value of the metric is then −1. A misalignment between the images results in small measurement values. This metric produces a cost function with sharp peaks and well-defined minima. The above metrics work identically for volumes. The number of spatial samples may be set empirically, e.g., to 50.

In the case of the prostate, after TRUS imaging the probe is retracted from the rectum, to avoid blocking seeds during fluoroscopy imaging. This causes the prostate to relax posteriorly, but usually without significant deformation. Practice guidelines specifically require slight rectal pressure, to mitigate deformation by probe translation during TRUS imaging. In this light, rigid registration should suffice. A 3D Euler transform of six parameters may be implemented, three parameters for the Euler angles that represent the rotation and three for the translational components. The center of rotation may be specified as the gravity center of the moving volume. Clinically, there is always an accurate and consistent initial guess for the registration. Standard patient positioning allows for estimating the main symmetry axes of the prostate, and alignment of the gravity centers of the TRUS volume and the seed cloud yields an accurate guess for translation.

One example of an evolution strategy that may be used is the "one plus one evolution strategy", denoted by (1+1)-ES. The step size adaptation may be performed according to a rule, such as, for example: if less than 20% of the generations are successful, then decrease the step size for the next generation; if more than 20% are successful, and then increase the step size in order to accelerate convergence. This adaptation is done for every N·LR generations, where N is the number of parameters to be optimized and LR is a constant which here is equal to one. All parameter values were set to default with the maximum number of iterations set to 100 and the minimum value for the Frobenius norm of the covariance matrix set to 0.0015. If the minimum value is smaller than this value, the optimization process will stop even before it hits the maximum iteration. The registration parameters were assigned initial weights corresponding to a 1 degree to 1 mm ratio for rotations and translations respectively. Of course, other values may be assigned to these parameters as desired for a given application or analysis.

Lastly, as TRUS and fluoroscopy are both likely to be spotted with false positives, the registration could be trapped in local minima. To counteract this potential problem, the registration may be restarted two or more times, each time slightly changing the initial pose (e.g., ±10% of last optimized parameter value), and then taking as a final solution the smallest root mean square results of the convergence optimizations.

An alternative to intensity-based volume-to-volume registration is intensity-based point-to-volume registration. Point-to-volume registration employs an algorithm that maps a discrete 3D point set from the C-arm fluoroscopy volume to a moving TRUS volume. Once again, the goal of the registration method is to find the set of parameters of the transformation that optimizes a specified metric. In point-to-volume, the 3D point cloud is considered as a fixed volume and the TRUS as a moving volume, and a transformation that maps the moving volume to the fixed volume with maximum similarity is sought. To each point in the cloud a voxel value is assigned and thus a black volume sparsely spotted with single white voxels is created. Each seed is represented by exactly one white voxel. In the embodiments described herein, two metrics were tested for point-to-volume: normalized correlation and mean squares metric (MS), the latter computing the square difference between the average moving volume intensity for an inside point and the average moving volume intensity for an outside point. The optimal value of the metric is zero. Poor matches between the images result in large values of the metric. The metric is not difficult to compute and has a relatively large capture radius. The number of pixels considered, N, may be set to the image size.

$$MS = \frac{1}{N} \sum_{i=1}^{N} (Img1_i - Img2_i)^2 \quad (b)$$

An inside point is defined as a point for which the corresponding value (in the point set node) is negative. An outside point is defined as a point for which the corresponding value (in the point set node) is positive. The transform and optimizer are kept the same as described in the above for volume-to-volume. Generally, point-to-volume is designed for schemes where each seeds is reconstructed into a single point, and seeds are represented as a list of points. To demonstrate the effectiveness of the methods described herein, they have been applied to ultrasound (US) and X-ray data of biological tissue; specifically, for use during treatment of prostate cancer using brachytherapy. The radioactive seeds implanted in the prostate during the procedure are features which provide enough information in both imaging technologies for intensity-based registration, thereby providing enough information for a technique such as MI to be used. These methods avoid problems such as noise, artifacts, and false positive appearances typically experienced when transrectal ultrasound (TRUS) is used alone. In initial studies conducted on a phantom prostate, intensity based registration between TRUS and CT/fluoroscopy imaging of prostate implants produced excellent results: Target reconstruction error (TRE) was consistently below clinical threshold, capture range was significantly larger than the initial guess guaranteed by the clinical workflow, robustness to false positive seed appearances was very good, and temporal performance was adequate. In contrast to all previous attempts to register US and fluoroscopy, the methods described herein perform the registration accurately, robustly, and automatically, and do not require pre-segmentation, user intervention, or any auxiliary instrumentation.

Pre-processing of image data may be required. For example, US, X-ray, and MRI data may be pre-processed with at least one filter based on an analysis with respect to space and/or frequency. Such an analysis may include one or more of:
(i) a statistical analysis;
(ii) a stochastic analysis;
(iii) a fractal analysis;
(iv) a wavelet analysis;
(v) a spectral analysis; and
(vi) array processing.
The result of the analysis may be a probability map, a probability score, intensity information, or a derivative thereof.

Examples of filters suitable for US, X-ray, and MRI data include, but are not limited to, window-level scaling, binary thresholding, a noise reduction filter, thresholding, averaging, median filtering, speckle reduction, diffusion filtering, anisotropic filtering, phase congruency, phase symmetry, gradient filtering, and contrast enhancement filtering. These may be used alone, or in various combinations, such as in series, parallel, or series-parallel combinations. In addition to the above, US data may also be subjected to beam profile filtering optionally in combination with any of the above.

As applied to prostate brachytherapy, the methods described herein provide major improvements in current practice of prostate cancer brachytherapy. Examples of such improvements include: (1) practical C-arm fluoroscopy for safe, simple, and robust intra-operative localization of brachytherapy sources relative to the prostate; (2) intra-operative dosimetry and implant optimization; and (3) exit dosimetry before the patient is released from the procedure room. Additionally, C-arm fluoroscopy-based exit dosimetry may also obviate CT-based post-implant dosimetry in the future. These benefits are expected to apply to all brachytherapy in general.

Insofar as the methods described herein exploit the spectral signature of ultrasonic reflections produced by "solid objects", i.e., seeds or markers, inside the material being imaged, it will be appreciated that the methods may be applied to any clinical application where suitable reflecting objects are present or are used, wherein registration of real-time C-arm fluoroscopy to other imaging modalities (such as, for example, CT or MRI) or to statistical anatomical atlases is required. For example, the reflectance of the pelvis may be applied in US-guided total hip replacement surgery, or the reflectance of bone fragments may be applied in US-guided bone fracture reduction (e.g., of the wrist, shoulder, etc.). In a similar manner, reflectance of the vertebra may be used in US-guided nerve root blocks, facet joint injection, and epidural injections. A further example is registration of a surgical tool or ablation tool in soft tissue images provided by US or MRI.

As used herein, the term "biological tissue" is intended to be inclusive of any tissue derived from an organism or part thereof, as well as a cell culture and a tissue culture. The biological tissue may be living or dead, and an analysis as described herein may be carried out on biological tissue in vivo or in vitro.

Embodiments of the invention may also be used for inspection and/or assessment of non-biological materials provided that suitable markers or seeds are available to be resolved in the imaging technologies used. Such applications may include inspection of materials for manufacturing and/or structural defects, analysis of effects of stress/strain on machine components, and detecting failure of machine components, in manufacturing, research, and industries such as transportation and aerospace. The markers or seeds may be already present in the materials (e.g., as an inherent feature of the materials), or they may be implanted in the materials prior to or during the inspection and/or assessment, or they may represent the defect location in the material itself.

Embodiments of the invention may also be used for inspection and/or assessment of combinations of biological tissues and non-biological materials provided that suitable markers or seeds are available to be resolved in the imaging technologies used. For example, the methods may be used during surgery to ensure accurate placement of prosthetic devices and minimally-invasive surgical tools, and/or after such procedures to confirm the placement and/or monitor the position or status of the implanted device. Application of the embodiments to other biological tissues and non-biological materials may require the implantation of markers or seeds the tissues or materials, or the tissues or materials may already include features which may serve as markers or seeds.

The embodiments described herein may be implemented in software, and may, for example, be made available as an add-on to imaging systems that are commercially available or currently in use, without adding auxiliary instrumentation and without imparting alterations in the basic clinical process. These features make it suitable for rapid and wide scale use, thus providing an immediate positive impact upon the thousands of patients undergoing brachytherapy and other relevant medical procedures every year.

The embodiments described herein may be implemented in a system including computer hardware, such as a computer-based system for use with imaging modalities to combine images from the imaging technologies by intensity-based registration of markers or seeds common to the images of the two modalities. The system may further include hardware associated with one or more imaging modalities, such as, for example, an ultrasound device, an X-ray device (e.g., fluoroscopy, CT), an MRI device, or a device related to a pre-implant plan of the material being imaged.

The following non-limiting examples are provided to further illustrate the invention.

Example 1

Methodology

1 Image Preprocessing

C-arm images were characterized by a low signal-to-noise ratio inducing image artifacts such as motion blur (i.e., object is blurred or smeared along the direction of relative motion). A 3-step filter and a line enhancement filter were implemented in order to enhance the fiducial and diminish the negative effects of artifacts. All filter parameter definitions are listed in Table 1 and explained below.

1.1 Filtering

1.1.1 Morphological Filtering

Morphological filtering was applied in grayscale to suppress the background of the C-arm image and enhance the FTRAC features. The structuring element chosen was in the shape of a disk of small radius, since the ball bearing and ellipse perimeter making up the FTRAC can be modeled as disk elements of small size. The morphological operator has only one filter parameter, which is the size of the structuring element.

1.1.2 Homomorphic Filtering

A homomorphic filter was used to de-noise the C-arm image. It sharpens features and flattens lighting variations in the image. The illumination component of an image was generally characterized by slow spatial variation while the reflectance component of an image tends to vary abruptly. These characteristics lead to associating the low frequencies of the Fourier transform of the natural log of an image with illumination and high frequencies with reflectance. See Kovesi [7] for details on the use of homomorphic filters. Even though these assumptions are an approximation at best, a good deal of control can be gained over the illumination and reflectance components with a homomorphic filter. For the homomorphic filter to be effective, it needs to affect the low- and high-frequency components of the Fourier transform differently. To compress the dynamic range of an image, the low frequency components need to be attenuated to some degree. At the same time, in order to enhance the contrast, the high frequency components of the Fourier transform needs to be magnified. Thus, Butterworth low and high pass filters were implemented and the image histograms were truncated accordingly.

TABLE 1

Filter parameter definitions and assigned values.

| Filter Definitions | Value |
|---|---|
| Three Step Filter | |
| A. Morphology filter | |
| Structuring element size (radius in pixels) | 2 |
| B. Homomorphic filter | |
| boost ratio of high frequency relative to low frequency | 2 |
| cutoff frequency of the filter | 0.05 |
| order for low and high pass Butterworth filters | 3 |
| truncation of the lower end of the image histogram | 5 |
| truncation of the higher end of the image histogram | 0.01 |
| C. Complex Shock Filter | |
| number of iteration | 10 |
| time step size | 1 |
| grid step size | 0.1 |
| magnitude of the complex diffusion in the gradient direction | 0.1 |
| amount of diffusion in the level set direction | 0.5 |
| slope of the aretangent | 0.3 |
| phase angle of the complex term (in radians) | $\pi/1000$ |

TABLE 1-continued

Filter parameter definitions and assigned values.

| Filter Definitions | Value |
|---|---|
| Line Enhancement Filter | |
| Frobenius norm factor (c) | 3 |
| Line-to-blob ratio ($\beta$) | 2 |
| Scale ($\sigma$) | 1 |

1.1.3 Complex Shock Filtering

Gilboa et al. [8] have developed a filter coupling shock and linear diffusion in the discrete domain. The shock filter's main properties are the following: (i) shocks develop at inflection points (i.e., second derivative zero-crossings), (ii) local extrema remain unchanged in time, (iii) the scheme is total variation preserving, (iv) the steady state (weak) solution is piece-wise constant, and (v) the process approximates deconvolution. Unfortunately, noise in the blurred signal will also be enhanced. Robustness to noise can be improved by convolving the signal's second derivative with a Laplacian of a Gaussian filter. This, however, is generally not sufficient to overcome the noise problem entirely, because convolving the signal with a Gaussian of moderate width in many cases will not cancel the inflection points produced by noise. In order to alleviate this problem, a more complex approach may be used: smoother parts may be denoised while edges are enhanced and sharpened. The complex shock filter may be given by:

$$I_t = -\frac{2}{\pi}\arctan\left(aIm\left(\frac{I}{\theta}\right)\right)|\nabla I| + \lambda I_{\eta\eta} + \tilde{\lambda} I_{\xi\xi} \quad (1)$$

where a is a parameter that controls the sharpness of the slope, $\lambda = re^{i\theta}$ is a complex scalar, $\tilde{\lambda}$ is a real scalar, $\xi$ is the direction perpendicular to the gradient, and $\eta$ is the direction of the gradient. In this way the inflection points are not of equal weight anymore; regions near edges with a large magnitude of second derivative near the zero crossing will be sharpened much faster than relatively smooth regions.

1.1.4 Line-Enhancement Filtering

We have recognized underlying synergy between enhancing parametric line fiducials in brachytherapy fluoroscopy images and enhancing contrast-filled blood vessels in digital subtraction angiography images. Vessel enhancement is typically used as pre-processing for maximum intensity projection display to improve on small vessel delineation. A multi-scale vessel enhancement technique was employed, using steerable filters to estimate local vessel orientation by an eigenvalue analysis in the Hessian matrix. To measure "vesselness" with a geometric interpretation, vessel enhancement as filtering that searches for tubular structures constrained within realistic limits of scale was used. In order to detect linear structures in the image, the second derivative with a Gaussian kernel at scale a produces a response of local intensities showing the contrast inside and outside the scale range in the direction of the derivative. This response kernel may be represented by the 2D Hessian matrix where its elements are the second partial derivatives of an image, which are obtained by the convolution of the Gaussian kernel at scale $\sigma$. The Hessian matrix is processed through eigenvalue analysis in order to extract the principal directions in which the second order object representation can be decomposed. Based on the direction relations of eigenvalues $\lambda 1$ and $\lambda 2$, linear objects can be detected as well as enhanced. For this example, the measure of fiducial lineness was expressed as:

$$v(x, \sigma) = \begin{cases} 0 & \text{if } \lambda_1 < 0 \\ \exp\left(-\frac{R_5^2}{2\beta^2}\right)\left(1 - \exp\left(\frac{-S^2}{2c^2}\right)\right) & \text{otherwise} \end{cases} \quad (2)$$

where $R_B$ differentiates lines from blobs. S is the Frobenius matrix norm to differentiate objects of interest from the background. The parameters $\beta$ and c are weighting factors determining the influence of $R_B$ and S. The result of this filter yields the probability of a pixel being a linear object. By fixing the scale, $\sigma$, and weighting factor, $\beta$, the dependence of 2D/3D registration may be narrowed to a single filter parameter, c, which influences the appearance of the object of interest with respect to the background. The filter enhancement weight factor influencing the Frobenius norm was set to c=3 from a test bed of c ∈ [2-5]. A higher weight (i.e., c=5) produced an image with low intensities and a faint outline of the FTRAC features whereas a smaller weight (i.e., c=2) degraded image contrast and allowed for neighboring structures to have similar intensities as the enhanced FTRAC. The line-to-blob ratio weight factor and scale were determined and set to $\beta$=2 and $\sigma$=1. For the DRR binary image Gaussian smoothing, the sigma value was set to $\sigma$=1.5 pixels.

1.2 Intensity-Based 2D/3D Registration

2D/3D registration was applied considering the DRR as the moving image and the C-arm image as the fixed image. MATLAB R2008a (The Math Works, Inc., Natick, Mass.) was used for implementation purposes. As only one C-arm image was used at a time, estimating the pose for that image was termed single-view registration, as explained by the flowchart in FIG. 2.

Metric: The normalized cross correlation metric that considers all pixel values in the images during registration was implemented. Fixed image pixels and their positions were mapped to the moving image. The correlation was normalized by the autocorrelations of both the fixed and moving images. The normalized cross correlation metric minimizes a cost function and the registration parameters are optimal when minimum cost is reached.

Transform: As the FTRAC is a rigid mechanical structure, rigid registration suffices. A transformation of six parameters was implemented, with three for Euler angles and three for translation.

Initial Guess: In the operating room, we have a consistently good initial guess for the registration. Standard patient positioning allows for aligning the main axes of the FTRAC, transrectal ultrasound (TRUS), and C-arm, enabling computation of gross registration in the anteriorposterior pose of the C-arm. Additional C-arm images were acquired according to a set protocol at 15° increments.

DRR Generation: The fiducial was projected on a two-dimensional binary image and blurred using a Gaussian filter. The parameter that needs to be considered during implementation is the Gaussian kernel set to a scale equal to 1.5$\sigma$ which allows sufficient blurring for the registration process to converge.

Optimizer: The CMA-ES is an evolutionary algorithm for difficult non-linear non-convex optimization problems in continuous domain. In contrast to quasi-Newton methods, the CMA-ES does not use or approximate gradients and does not even presume or require their existence. This makes the method applicable to non-smooth and even non-continuous problems, as well as to multimodal and/or noisy problems.

The CMA-ES has several invariance properties. Two of them, inherited from the plain evolution strategy, are (i) invariance to order preserving (i.e., strictly monotonic) transformations of the objective function value, and (ii) invariance to angle preserving (rigid) transformations of the search space (including rotation, reflection, and translation), if the initial search point is transformed accordingly. The CMA-ES does not require a tedious parameter tuning for its application. With the exception of population size, tuning of the internal parameters is not left to the user.

Example 2

Registration Evaluation

An objective of this example is to provide an estimation of the C-arm fluoroscope poses for subsequent brachytherapy implant reconstruction. What follows is that if the tissue/organ of interest (e.g., prostate) is kept near the isocenter, projection and reconstruction are both insensitive to depth. In this example, the values for mean registration error and standard deviations were calculated as the difference obtained from the ground truth and the registration, respectively.

Ground-Truth and Optimization

The method of Example 1 was tested using the FTRAC fiducial described by Jain et al. [5]. Following precise segmentation of the FTRAC motifs, their algorithm described allowed for an average registration accuracy of 0.56 mm and 0.33°, which were validated in controlled phantom experiments and accepted it as ground-truth. 111 clinical C-arm images from 13 patients were acquired under ethics board approval, during prostate brachytherapy procedure, with the FTRAC fiducial in the field of view.

An OEC 9800 C-arm fluoroscope (GE Healthcare, UK) was fully calibrated and images dewarped as prescribed by Lee et al. [9]. The imaging range was within a half cone of 20° around the AP position. Capture range was defined as the range within which the algorithm is more likely to converge to the correct optimum. Random misalignment of maximum ±10 mm translation and ±10 degree rotation was applied to ground truth obtained by segmenting the FTRAC and recovering pose. This capture range, especially for rotation, is larger than the error of the initial guess one can achieve clinically. The number of iterations for the optimizer was set to 30 and the population size at 65, resulting in 98.5% algorithm convergence.

Clinical Patient Data Results

The filter parameters for both the three-step filter and line enhancement filter were determined empirically by using a subsample of 10 C-arm images, with varying initial contrast, and fine tuning the values so that the FTRAC features are always enhanced with respect to their neighborhood. From FIG. 3-left, it can be observed that image contrast differs between patients. However, the chosen filter parameters improved the robustness and performance of the filter; the pelvic bone and other neighboring structures were suppressed successfully while both the FTRAC fiducial and implanted seeds were enhanced.

Using the Three-Step Filler

Figure 3:
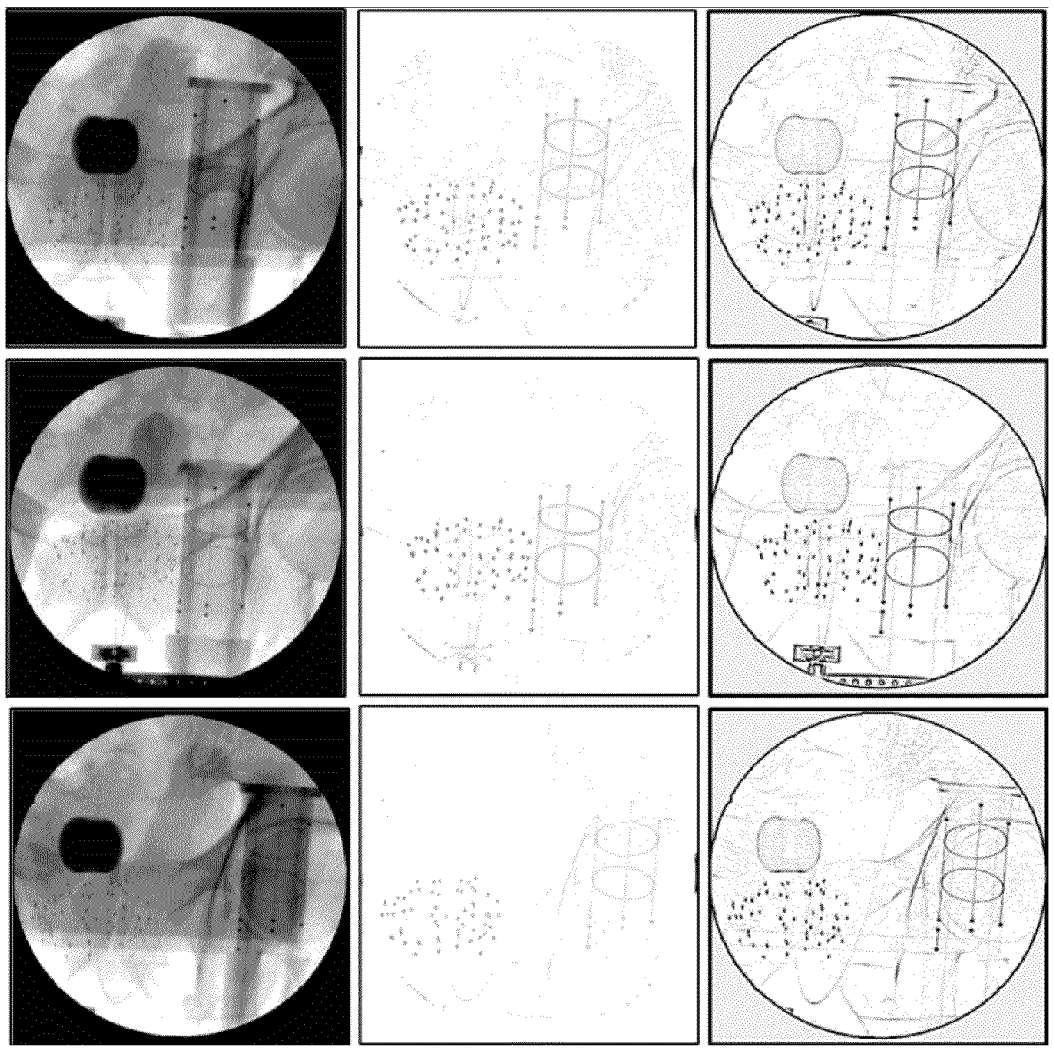
FIG. 3 shows image preprocessing techniques applied to image data for a prostate brachtherapy procedure: (left) example clinical images from with varying contrast; (center) 3-step filter with 13 control parameters; and (right) the line enhancement filter using a single control parameter.

The performance of the filter is presented in FIG. 3-center. The filtered C-arm image was given as input to the intensity-based registration algorithm. From Table 2, five of the six degrees of freedom parameters were consistently below 0.5 mm and 1°. The average rotation and translation errors were 0.62° (std=0.31°) and 0.72 mm (std=0.55 mm), respectively. As expected, the single view registration process did not recover the depth robustly (Tz parameter), yet on average the value is below clinical requirement of 2 mm. For the unoptimized MATLAB prototype implementation, a typical registration took about 170 seconds per image with Intel 340 Core2, 2.4 GHz, dual-core computer.

TABLE 2

Pose estimation results using the 3-Step filter.
±10 mm and ±10° perturbation

| Tx (mm) | Ty (mm) | Tz (mm) | Rotations (degree) |
|---|---|---|---|
| 0.14 ± 0.08 | 0.11 ± 0.16 | 1.9 ± 1.4 | 0.62 ± 0.31 |

Using the Line Enhancement Filler

FIG. 3-right shows the performance of the line enhancement filter. In order to speed up the registration process when compared to the 3-step filtering scheme, the C-arm images were automatically cropped by half and retained the right-side of the image only since the fiducial was consistently positioned in this region from existing clinical protocol. From Table 3, the average rotation and translation errors were 0.67° (std=0.40°) and 0.87 mm (std=0.27 mm) respectively.

TABLE 3

Pose estimation results using the Line enhancement filter.
±10 mm and ±10° perturbation

| Tx (mm) | Ty (mm) | Tz (mm) | Rotations (degree) |
|---|---|---|---|
| 0.21 ± 0.21 | 0.11 ± 0.12 | 2.2 ± 0.5 | 0.67 ± 0.40 |

Figure 4:
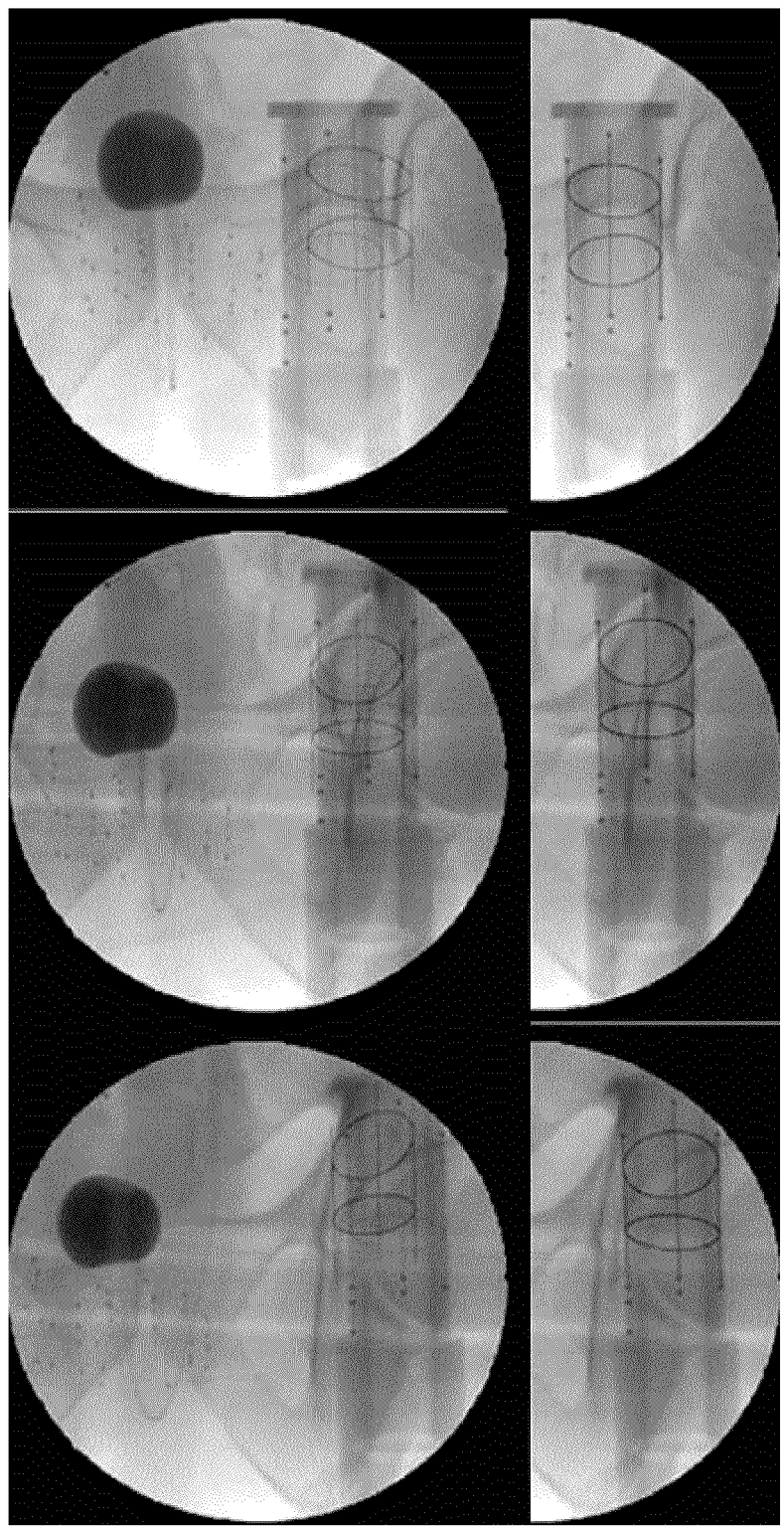
FIG. 4 shows sample images for data for a prostate brachtherapy procedure before (left) and after (right) registration, with accurate superposition of the FTRAC fiducial using a line enhancement filter.

FIG. 4 shows sample images for data for a prostate brachtherapy procedure before (left) and after (right) registration, with accurate superposition of the FTRAC fiducial using a line enhancement filter.

DISCUSSION AND CONCLUSION

The recovered pose using both filtering schemes yielded mean accuracies within ±1° rotation and ±1 mm in lateral translation which should yield subsequent accurate 3D reconstruction of prostate brachytherapy seeds. Less than 6% of total runs registration trials executed failed due to the FTRAC fiducial being positioned near the black circular mask of the C-arm images, meaning that some features such as the top ball bearings and part of the top ellipse were not visible in the image. Also, since the registrations were started from a random initial guesses, some runs were launched from an initial guess that projected the FTRAC outside the fluoroscopy image into the black mask where there was no feature to guide the optimization into the image. Registration was not rerun with a new initial guess since the purpose of the study was to show the true viability and robustness of the registration algorithm in a single run. It is expected that pose recovery results will improve with restarting the registration process and/or with launching from an initial guess that projects the FTRAC within the C-arm image.

The contents of all references, pending patent applications, and published patents cited throughout this application are hereby expressly incorporated by reference.

EQUIVALENTS

Those skilled in the art will recognize or be able to ascertain variants of the embodiments described herein. Such variants are within the scope of the invention and are covered by the appended claims.

REFERENCES

1. R. Sindwani and R. D. Bucholz, "The next generation of navigational technology," Otolaryngol. Clin. North Am. 38(3), 551-562, 2005.
2. R. L. Galloway, "The process and development of image-guided procedures," Annu. Rev. Biomed. Eng. 3, 83-108, 2001.
3. Z. Yaniv and K. Cleary, "Image-guided procedures: A review," Computer Aided Intervention and Medical Robotics, Georgetown University, Imaging Science and Information Systems Center, Washington, D.C., Paper No. TR 2006-3, 2006.
4. S. Nithiananthan, K. K. Brock, J. C. Irish, and J. H. Siewerdsen, "Deformable registration for intra-operative cone-beam CT guidance of head and neck surgery," IEEE Proceedings of Engineering in Medicine and Biology Society, 1, pp. 3634-3637, 2008.
5. 26A. K. Jain, T. Mustufa, Y. Zhou, et al., "FTRAC—a robust fluoroscope tracking fiducial." Medical physics; 32(10), pp. 3185-98, 2005.
6. A. K. Jain, A. Deguet, I. Iordachita, et al., "Intra-operative Guidance in Prostate Brachytherapy Using an Average Carm." MICCAI 2007, Lecture Notes in Computer Science, 4792, pp 9-16, 2007.
7. P. Kovesi. Functions for Computer Vision and Image Processing., 2009. Online: http://www.csse.uwa.edu.au/~pk/research/matlabfns/.
8. G. Gilboa, N. Sochen, and Y. Zeevi. "Regularized shock filters and complex diffusion." Proc ECCV pp. 399-413, 2002.
9. Lee J; Liu X, Jain A K, et al.: Prostate brachytherapy seed reconstruction with Gaussian 590 blurring and optimal coverage cost. IEEE Trans Med Imaging, 28(12):1955-68 (2009).
10. Mattes D., Haynor D. R., Vesselle H., Lewellen T. and Eubank W. Nonrigid multimodality image registration. Proc. SPIE Medical Imaging: pp. 1609-1620, 2001.
11. Mattes D, Haynor D R, Vesselle H, Lewellen T K, Eubank W. "PET-CT image registration in the chest using free-form deformations," IEEE Trans. Medical Imaging, 22(1): 120-128 (2003).

The invention claimed is:

1. A method for estimating X-ray pose, comprising:
resolving a coordinate system in a single 2D X-ray image of a material under investigation; and
applying intensity-based 2D/3D registration without segmentation to the coordinate system 2D X-ray image and an ultrasound image volume of the material under investigation or a known 3D model of the coordinate system;
wherein the coordinate system is associated with the material under investigation;
wherein the intensity-based 2D/3D registration yields an estimate of the X-ray pose.

2. The method of claim 1, wherein the coordinate system is provided by introducing one or more markers with the material under investigation.

3. The method of claim 2, wherein introducing one or more markers is associated with a therapeutic procedure or a medical intervention.

4. The method of claim 3, wherein the ultrasound image volume is obtained from transrectal ultrasound.

5. The method of claim 2, including iteratively updating locations of markers and using those marker locations to compute pose.

6. The method of claim 3, wherein introducing one or more markers comprises implanting, attaching, or fixing one or more markers to a tissue or an organ of interest.

7. The method of claim 1, wherein the coordinate system is provided by introducing a fiducial.

8. The method of claim 1, wherein intensity based registration includes filtering the X-ray image to simultaneously enhance coordinate system features and suppress neighbouring structures.

9. The method of claim 8, wherein filtering the X-ray image comprises using one or more filters.

10. The method of claim 8, wherein filtering the X-ray image comprises applying a three-step filter and a line enhancement filter.

11. The method of claim 10, wherein the three-step filter includes a morphological filter, a homomorphic filter, and a complex shock filter.

12. The method of claim 1, wherein processing images comprises applying an imaging-blurring filter.

13. The method of claim 1, wherein the images are associated with a medical intervention.

14. The method of claim 13, wherein the images are associated with a brachytherapy procedure.

15. The method of claim 13, wherein the brachytherapy procedure is associated with treating prostate cancer.

16. The method of claim 1, wherein the X-ray images include markers.

17. The method of claim 16, wherein the markers are selected from radioactive seeds and surgical clips.

18. The method of claim 1, wherein the coordinate system is provided by an inherent feature of a material under investigation.

19. The method of claim 1, wherein the X-ray image is a fluoroscopy is image.

20. Programmed media for use with a computer and with X-ray image data and ultrasound image data, the programmed media comprising:
  a computer program stored on non-transitory storage media compatible with the computer, the computer program containing instructions to direct the computer to:
  receive X-ray image data and ultrasound image data, the X-ray image data including a coordinate system associated with a material under investigation;
  apply intensity-based 2D/3D registration without segmentation to the coordinate system in a single 2D X-ray image and an ultrasound image volume of the material under investigation or known 3D model of the coordinate system, wherein the intensity-based registration yields an estimation of the X-ray pose; and
  output the estimation of the X-ray pose.

21. The programmed media of claim 20, wherein the ultrasound image data is transrectal ultrasound image data.

22. The programmed media of claim 20, wherein the X-ray image is a fluoroscopy image.

* * * * *